US006984498B2

(12) United States Patent
Adair

(10) Patent No.: US 6,984,498 B2
(45) Date of Patent: *Jan. 10, 2006

(54) METHOD OF CANCER SCREENING PRIMARILY UTILIZING NON-INVASIVE CELL COLLECTION, FLUORESCENCE DETECTION TECHNIQUES, AND RADIO TRACING DETECTION TECHNIQUES

(76) Inventor: Edwin L. Adair, 317 Paragon Way, Castle Pines Village, CO (US) 80104

( * ) Notice: Subject to any disclaimer, the term of this patent is extended or adjusted under 35 U.S.C. 154(b) by 0 days.

This patent is subject to a terminal disclaimer.

(21) Appl. No.: 10/836,464

(22) Filed: Apr. 30, 2004

(65) Prior Publication Data
US 2004/0202612 A1 Oct. 14, 2004

Related U.S. Application Data

(63) Continuation-in-part of application No. 10/176,558, filed on Jun. 21, 2002, now Pat. No. 6,750,037, which is a continuation-in-part of application No. PCT/US00/34121, filed on Dec. 16, 2000, which is a continuation of application No. 09/472,945, filed on Dec. 27, 1999, now Pat. No. 6,190,877.

(51) Int. Cl.
C12Q 1/02 (2006.01)
C12Q 1/00 (2006.01)
G01N 33/53 (2006.01)

(52) U.S. Cl. .............................. 435/29; 435/968; 435/4
(58) Field of Classification Search .................. 435/29, 435/4, 968
See application file for complete search history.

(56) References Cited

U.S. PATENT DOCUMENTS 3,394,369 A   7/1968   Johnston, Jr. ................. 47/58
3,846,490 A   11/1974  Aronova et al. ............. 562/567
3,973,129 A   8/1976   Blumberg et al. ......... 250/461 B
4,772,691 A   9/1988   Herman ....................... 540/145
4,886,831 A   12/1989  Morcos et al. .............. 514/456
4,897,444 A   1/1990   Brynes et al. .............. 525/54.1
4,905,670 A   3/1990   Adair ........................... 128/18
4,920,143 A   4/1990   Levy et al. .................. 514/410
4,977,177 A   12/1990  Bommer et al. ............ 514/410
4,997,639 A   3/1991   Aizawa et al. .................. 424/9
5,026,368 A   6/1991   Adair ........................... 606/15
5,043,101 A   8/1991   Gordon ..................... 252/408.1
5,079,262 A   1/1992   Kennedy et al. ............ 514/561

(Continued)

FOREIGN PATENT DOCUMENTS
EP       0 277 837       10/1988

(Continued)

OTHER PUBLICATIONS

Abstract, Mu Y, et al., "P-S-D-007 Luminescence in the Diagnosis of Exfoliative Cells from Malignant Tumors", X-P-0021614131, vol. 9, No. 4, 1987, pp. 258-259.

(Continued)

Primary Examiner—Louise N. Leary
(74) Attorney, Agent, or Firm—Sheridan Ross PC

(57) ABSTRACT

A cancer screening method is provided, wherein the method is characterized by administering a compound to a patient, the compound being a complex of a fluorescent marker and a radioactive marker, in a dose emitting between 5 Gy and 20 Gy radiation. Cells are then collected preferably through non-invasive or minimally invasive means. If fluorescence is observed in the exfoliated cells, tomographic scanning is conducted to further locate and/or confirm suspected malignant areas or metastatic areas. Further observation or treatment may be conducted either through fluorescence guided endoscopy, photo-dynamic therapy, and/or radiation treatment.

4 Claims, 4 Drawing Sheets

U.S. PATENT DOCUMENTS

| | | | |
|---|---|---|---|
| 5,087,636 A | 2/1992 | Jamieson et al. | 514/410 |
| 5,117,466 A | 5/1992 | Buican et al. | 382/6 |
| 5,122,453 A | 6/1992 | Martin et al. | 435/7.24 |
| 5,143,054 A | 9/1992 | Adair | 128/18 |
| 5,149,708 A | 9/1992 | Dolphin et al. | 514/410 |
| 5,162,231 A | 11/1992 | Cole et al. | 436/64 |
| 5,211,938 A | 5/1993 | Kennedy et al. | 424/7.1 |
| 5,234,940 A | 8/1993 | Kennedy et al. | 514/410 |
| 5,251,613 A | 10/1993 | Adair | 128/6 |
| 5,270,171 A | 12/1993 | Cercek et al. | 435/29 |
| 5,283,255 A | 2/1994 | Levy et al. | 514/410 |
| 5,308,608 A | 5/1994 | Dolphin et al. | 424/9 |
| 5,308,861 A | 5/1994 | Aizawa et al. | 514/410 |
| 5,391,547 A | 2/1995 | Cole et al. | 514/184 |
| 5,418,169 A | 5/1995 | Crissman et al. | 436/94 |
| 5,422,093 A | 6/1995 | Kennedy et al. | 424/9.61 |
| 5,441,531 A | 8/1995 | Zarate et al. | 607/90 |
| 5,554,505 A | 9/1996 | Hajek et al. | 435/721 |
| 5,556,764 A | 9/1996 | Sizto et al. | 435/7.24 |
| 5,591,422 A | 1/1997 | Hemmi et al. | 424/9.362 |
| 5,605,805 A | 2/1997 | Verwer et al. | 435/7.24 |
| 5,616,342 A | 4/1997 | Lyons | 424/450 |
| 5,627,040 A | 5/1997 | Bierre et al. | 435/7.24 |
| 5,652,114 A | 7/1997 | Chu et al. | 435/7.23 |
| 5,773,609 A | 6/1998 | Robinson et al. | 540/145 |
| 5,955,490 A | 9/1999 | Kennedy et al. | 514/410 |
| 6,190,877 B1 * | 2/2001 | Adair | 435/29 |
| 6,235,767 B1 | 5/2001 | Kelly et al. | 514/410 |
| 6,316,215 B1 * | 11/2001 | Adair et al. | 435/29 |
| 6,358,989 B1 | 3/2002 | Kunz et al. | 514/411 |
| 6,387,350 B2 | 5/2002 | Goldenberg | 424/1.57 |
| 6,395,016 B1 | 5/2002 | Oron et al. | 607/88 |
| 6,422,988 B1 | 7/2002 | Bradshaw et al. | 600/3 |
| 6,422,989 B1 | 7/2002 | Hektner | 600/3 |
| 6,566,517 B2 | 5/2003 | Miura et al. | 540/145 |
| 6,750,037 B2 * | 6/2004 | Adair et al. | 435/29 |

FOREIGN PATENT DOCUMENTS

JP 04330013 A 11/1992

OTHER PUBLICATIONS

Abstract, Schwartz, G., et al., "Selected Amino Acridines as Fluorescent Probes in Cytochemistry in General and in the Detection of Cancer Cells in Particular", *Analytical and Quantitative Cytology*, vol. 4, No. 1, 1982, pp. 44-54.

Abstract, Gardiner, R.A., et al., "Abnormal prostatic cells in ejaculates from men with prostatic cancer: A preliminary report", *British Journal of Urology*, vol. 78, No. 3, 1996, pp. 414-418.

Abstract, Bologna, M., et al., "Improved tissue culture method for the study of prostatic carcinoma: A significant diagnostic tool.", *Pathology Research and Practice*, vol. 191, No. 9, 1995, pp. 899-903.

Artemov et al., *Cancer Res.*, 61:3039-3044 (2001).

Fiel et al., *Cancer Letters*, 40:23-32 (1988).

Furmanski and Longley, *Cancer Res.*, 48:4604-4610 (1988).

Harisinghani et al., *N. Engl. J. Med.*, 348(25):2491-2499 (2003).

Koenig et al., *Magnetic Resonance in Medicine*, 4:252-260 (1987).

Lyon et al., *Magnetic Resonance in Medicine*, 4:24-33 (1987).

Rosenthal et al., *Clin. Cancer Res.*, 5:739-745 (1999).

van Zijl et al., *Acta Radiologica*, 374(supp):75-79 (1990).

Pottier et al.; "Non-Invasive Technique for Obtaining Fluorescence Excitation and Emission Spectra *In Vivo*"; *Photochemistry and Photobiology*; vol. 44, No. 5; pps. 679-687, 1986.

Abstract, Sauter, E.R., et al., "Nipple aspirate fluid: A promising non-invasive method to Identify cellular markers of breast cancer risk", *British Journal of Cancer*, vol. 76, 1997, pp. 494-501.

Abstract, Sugiyama, M., et al., "Non-invasive detection of bladder cancer by identification of abnormal CD44 proteins in exfoliated cancer cells in urine", Abstract, *Clinical Molecular Pathology*, 1995, vol. 48, pp. M142-M147.

Nyamekye et al.; "Photodynamic Therapy of Normal and Ballon-Injured Rat Carotid Arteries Using 5-Amino-Levulinic Acid"; *Circulation*, vol. 91, No. 2, Jan. 15, 1995, pp. 417-425.

Peng et al.; "5-Aminolevulinic Acid-Based Photodynamic Therapy"; *American Cancer Society*; 1997; pp. 2282-2305.

Berg et al.; "The Influence of Iron Chelators On the Accumulation of Protoporphyrin IX in 5-Aminolaevulinic Acid-Treated Cells"; *British Journal of Cancer*; 1996; pp. 688-697.

Noodt et al.; "Apoptosis and Necrosis Induced With Light and 5-Aminolaevulinic Acid-Derived Protoporphyrin IX"; *Flow Cytometry*; 1996; pp. 22-29.

Malik et al.; "Destruction of Erythroleukaemic Cells by Photoactivation of Endogenous Porphyrins" *British Journal of Cancer*; 1987; 56; pp. 589-595.

Leon et al.; "Localized Intracoronary Gamma-Radiation Therapy to Inhibit the Rcurrence of Restenosis After Stenting"; *The New England Journal of Medicine*; Jan. 25, 2001; 344(4); pp. 250-256.

Verin et al.; "Endoluminal Beta-Radiation Therapy for the Prevention of Coronary Restenosis After Balloon Angioplasty"; *The New England Journal of Medicine*; Jan. 25, 2002; 344(4); pp. 243-249.

Abstract: Leunig et al.; "Fluorescence Photodetection of Neoplastic Lesions in the Oral Cavity Following Topical Application of 5-Aminolevulinic Acid"; *Laryngo-Rhino-Otologie*; vol. 75, No. 8, Aug. 1996; pp. 459-464.

Firnau et al.; "$^{64}$Cu Labelling of Hematoporphyrin Derivative for Non-Invasive In-Vivo Measurements of Tumour Uptake" *Porphyin Localizatikon and Treatment of Tumors*; 1984 Alan R. Liss, Inc.; pp. 629-636.

Webster's II New Riverside University Dictionary, Copyright 1984, 1988, 1994, pp. 490 and 968.

News and Views; Radiolabelled photosensitizers for tumour imaging and photodynamic therapy, B.C. Wilson and J.E. VanLier; XPOO8023295, 459-463.

The Biological Characteristics of a Water Solube Porphyrin in Rat Lymph Nodes; D.A. Cole, J.A. Mercer-Smith, S.A. Schreyer, J.K. Norman and D.K. Lavallee; XP008023296, 457-464.

Porphyrin Localization and Treatment of Tumors, pp. 629-636; 1984 Alan R. Liss, Inc., XP0080239292.

Chromatographic Analysis and tissue Distribution of Radiocopper-Labelled Haematoporphyrin Derivatives; Brian C. Wilson, Gunter Firnau, W. Patrick Jeeves, Kay L. Brown, Diane M. Bums-McCormick; XP008023291, 72-79.

* cited by examiner

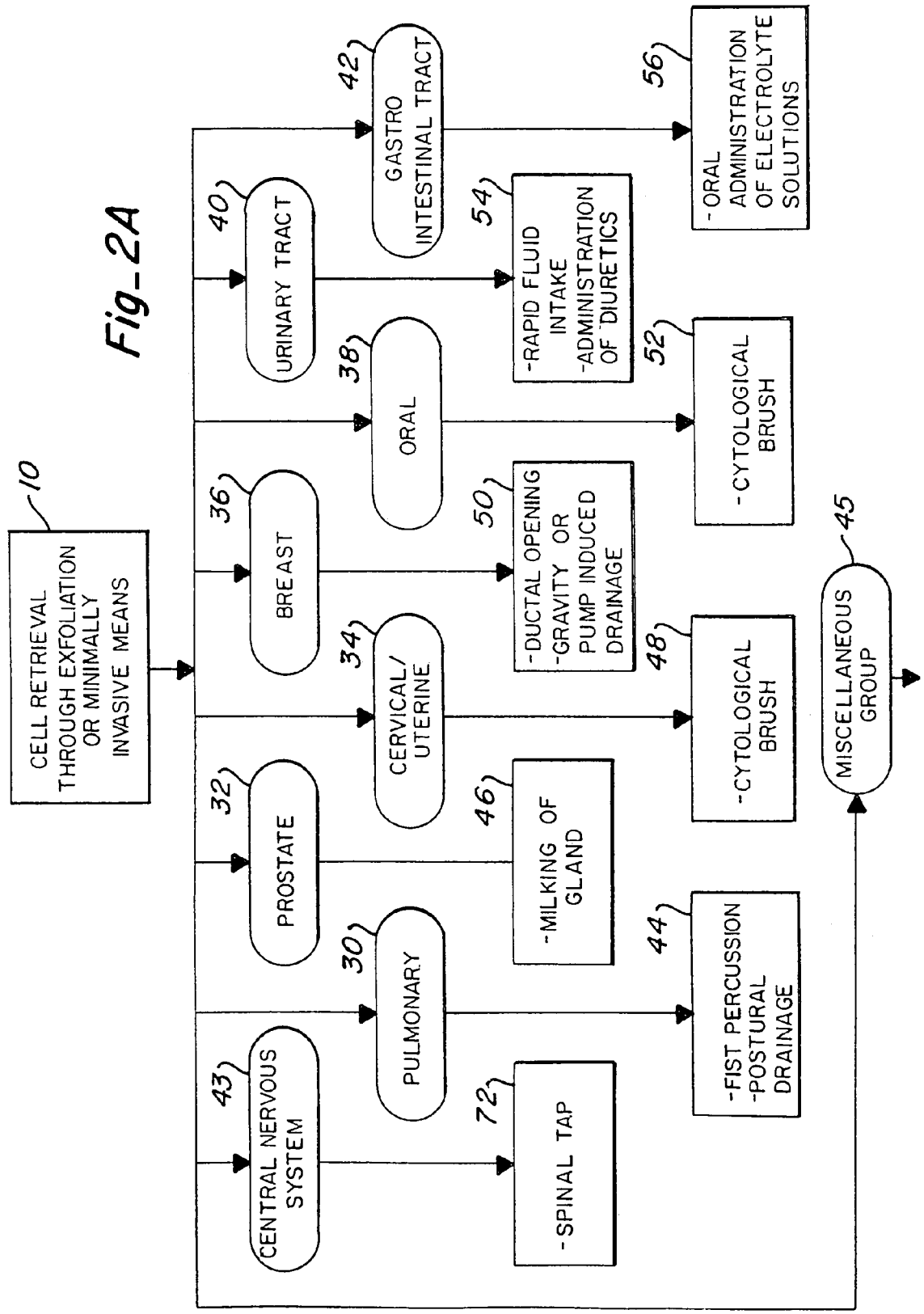
Fig_2A

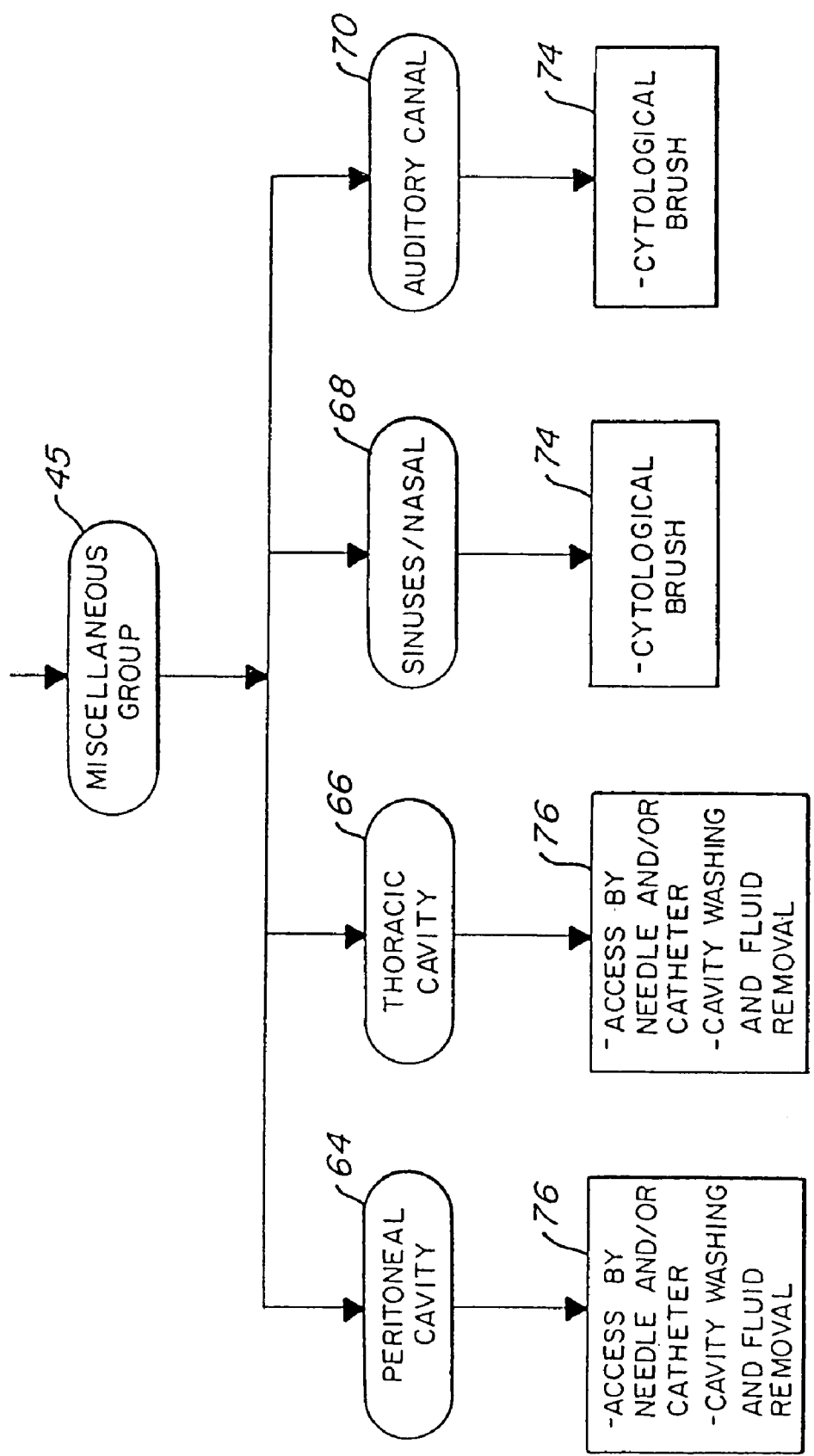
Fig_2B

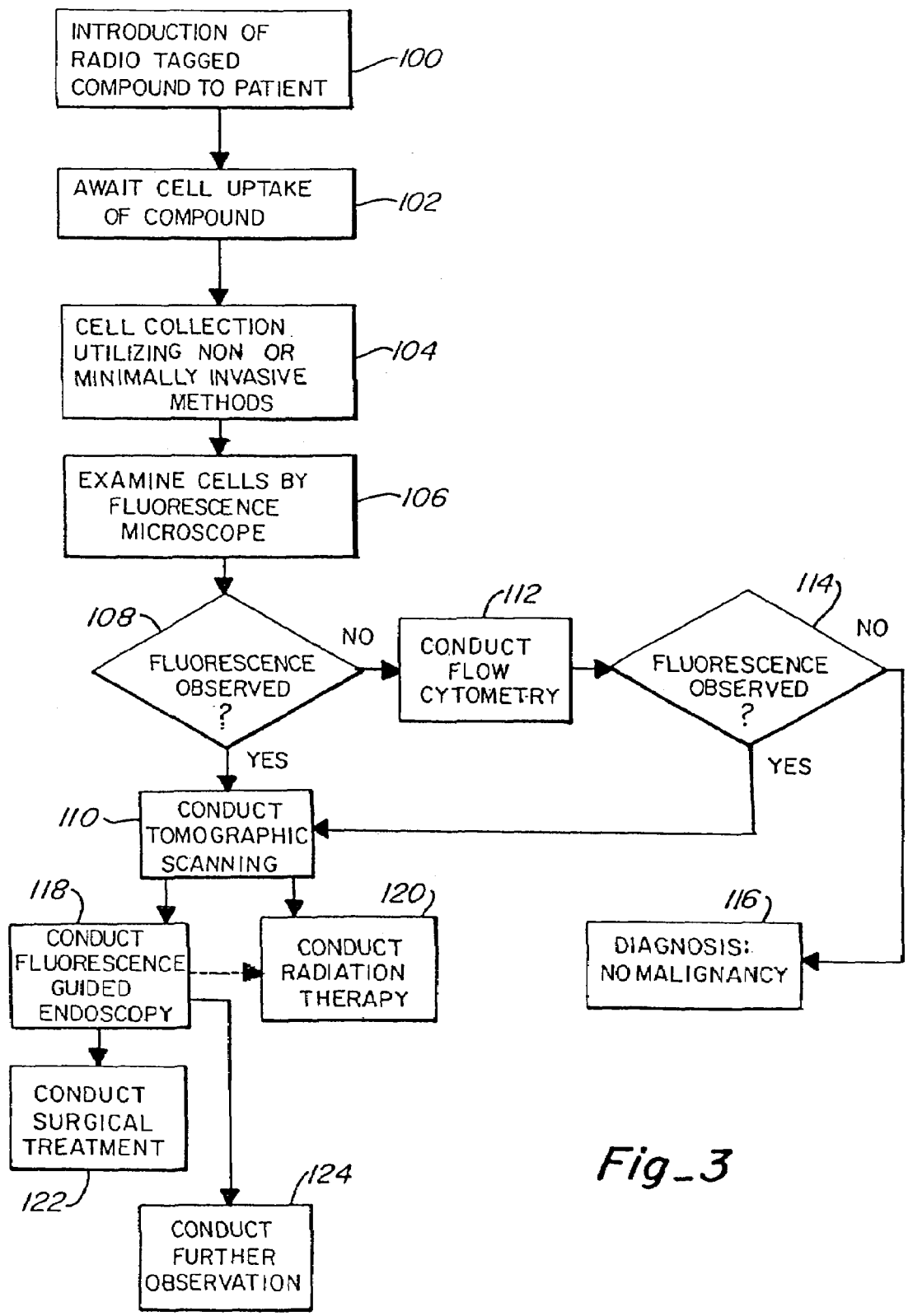
Fig_3

METHOD OF CANCER SCREENING PRIMARILY UTILIZING NON-INVASIVE CELL COLLECTION, FLUORESCENCE DETECTION TECHNIQUES, AND RADIO TRACING DETECTION TECHNIQUES

CROSS REFERENCE TO RELATED APPLICATION

This application is a continuation-in-part of U.S. patent application Ser. No. 10/176,558 filed Jun. 21, 2002 U.S. Pat. No. 6,750,037 which is a continuation-in-part of co-pending PCT application Ser. No. PCT/US00/34121 filed on Dec. 16, 2000, which is a continuation of U.S. patent application Ser. No. 09/472,945, filed on Dec. 27, 1999, now U.S. Pat. No. 6,190,877.

TECHNICAL FIELD

This invention relates to a method of cancer screening and, more particularly, to a method primarily utilizing non-invasive cell collection techniques, and a combination of fluorescence detection techniques and radio tracing techniques for positive identification of malignant cells.

BACKGROUND ART

There are a number of prior art methods and apparatuses which are used in the detection and treatment of cancer. Fluorescent markers have been used to help identify cancerous tissue within a patient. Radio tracers or markers have also been used in the detection and treatment of cancer. There are also a number of prior art methods and apparatuses which relate to flow cytometry and the act of segregating and counting malignant cells within a tissue sample.

One example of a prior art reference which discloses the use of fluorescence detection for cancer screening is U.S. Pat. No. 5,270,171 to Cercek, et al. This reference teaches a method to identify, separate and purify the factor or factors that provoke a response by SCM (structuredness of the cytoplasmic matrix) responding lymphocytes. The use of such purified factor or factors enhances a SCM cancer screening test. The SCM is a peptide of at least nine amino acid residues. The residues produce at least a 10% decrease in the intracellular fluorescence polarization value of SCM responding lymphocytes from donors afflicted with cancer. Antibodies specific for the SCM factor are useful in immunoassays that can detect the factor, including detection of cancer cells grown in vitro. The SCM factor is useful for screening of blood samples and other body fluids or cell aspirates for the presence of malignancy in the donor. A method is also disclosed for testing lymphocytes obtained from the donor for presence or absence of a malignancy. A further method is also disclosed for screening a blood sample for the presence of a malignancy in a body of a donor.

U.S. Pat. No. 5,391,547 discloses a method of using porphyrins to detect lung cancer, and more particularly, to the use of tetra-aryl porphyrins. The porphyrins are used as a fluorescent tracer for cancers of the lung. The porphyrins may be complexed with Copper 64 ($^{64}$Cu) or Copper 67 ($^{67}$Cu). Thus, the complex can be used as radio tracers as well. The $^{67}$Cu provides a source of beta radiation for selective destruction of lung malignancies as well as gamma radiation useful for image analysis, as by single photon emission compute tomography. The $^{64}$Cu may be used for radio tracing wherein a positron emission tomography technique can be used to locate the malignant tissue.

U.S. Pat. No. 5,562,114 to Chu, et al. discloses a diagnostic immunoassay method using monoclonal antibodies. These monoclonal antibodies are capable of identifying an antigen associated with carcinomas of ductal lineage and can be used both diagnostically and therapeutically. More specifically, the monoclonal antibodies of this reference are capable of targeting the breast carcinoma cells in vivo. The monoclonal antibodies are purified and are labeled with radioactive compounds, for example, radioactive iodine, and then are administered to a patient intravenously. After a localization of the antibodies at the tumor site, they can be detected by emission, tomographical and radio nuclear scanning techniques thereby pinpointing the location of the cancer.

U.S. Pat. No. 5,087,636 to Jamieson, et al. discloses a method to identify and destroy malignant cells in mononuclear cell populations. This method includes the steps of contacting a composition of bone marrow cells or other cells with a green porphyrin of a specific compound, irradiating the cell composition with light at a wave length effective to excite fluorescence of the green porphyrin, and then detecting the presence or absence of fluorescence indicating malignancy. This reference also discloses the steps by which the bone marrow cells are removed, separated, washed and diluted to an appropriate concentration for treatment, incubated, centrifuged, and exposed to the irradiating light.

U.S. Pat. Nos. 5,308,608 and 5,149,708 to Dolphin, et al. disclose specific types of porphyrin compounds which may be used for detection, photosensitization, or the destruction of a targeted biological material when the targeted tissue is contacted with the specified porphyrin, and irradiated with light that excites the compound.

U.S. Pat. No. 5,211,938 to Kennedy, et al. discloses a method of detection of malignant and non-malignant lesions by photo chemotherapy of protoporphyrin IX precursors. 5-amino levulinic acid (5-ALA) is administered to the patient in an amount sufficient to induce synthesis of protoporphyrin IX in the lesions, followed by exposure of the treated lesion to a photo activating light in the range of 350–640 nanometers. Naturally occurring protoporphyrin IX is activatable by light which is in the incident red light range (600–700 nanometers) which more easily passes through human tissue as compared to light of other wave lengths which must be used with other types of porphyrins. In short, the use of 5-ALA makes cell fluorescence easier to observe, and also greatly reduces the danger of accidental phototoxic skin reactions in the days following treatment since protoporphyrin IX precursors have a much shorter half life in normal tissues than other popularly used porphyrins.

Another set of references exists which relate to flow cytometry utilizing fluorescence producing compounds. One such prior art reference includes U.S. Pat. No. 5,605,805 to Verwer, et al., which discloses a method for determining the lineage of acute leukemia cells in the sample by fluorocytometry. Other examples of fluorocytometry utilizing fluorescence include U.S. Pat. No. 5,418,169 to Crissman, et al., U.S. Pat. No. 5,556,764 to Sizto, et al., and U.S. Pat. No. 5,627,040 to Bierre.

Present methods relating to cancer screening using fluorescence detection systems require the use of interventional devices such as endoscopes which have the special capability of delivering specified light frequencies to a targeted area within a patient. These endoscopes illuminate the targeted part of the body in which cancer is suspected. The light delivered at a specified frequency illuminates an area which has previously been subjected to some type of fluorescent marker, such as a porphyrin which causes malignant cells to illuminate or fluoresce under observation of light at a specified frequency. In all cases, introduction of an endoscope into the body requires some type of sedation or general or local anesthesia. Once a tumor has been located by use of the interventional device, depending upon the type of tumor, photo chemotherapy or other treatment means can be used. However, prior to actual treatment, there must be a confirmed test of cancer. Accordingly, the tumor still needs to be sampled by an appropriate biopsy method. Generally, biopsy methods also require some type of sedation or anesthesia. Thus, traditional methods of confirming a malignancy may require at least two interventional surgical procedures.

While each of the foregoing references may be adequate for their intended purposes, many of these inventions require surgical techniques to remove the cell samples which can be traumatic to the patient. Furthermore, many of the references require complex equipment, and special medical expertise in order to conduct the procedures and to make the diagnoses. Therefore, there is a need for a reliable cancer screening technique or method which can test for cancer in a wide variety of cells and which may be accomplished by non-invasive or minimally invasive cell collection techniques which limit patient trauma, are inexpensive to conduct, and can be confirmed positively by a pathologist, oncologist or other physician without additional testing or screening. There is also a need for a reliable cancer screening technique or method which can utilize two different types of screening technologies within a single cancer screening procedure, therefore improving the ability to make a diagnosis of cancer, and also to provide a follow-on treatment of the cancer, either through photo-dynamic therapy and/or through radiation-treatment. The invention described below provides each of these advantages, among others, which will be apparent to those skilled in the art.

DISCLOSURE OF THE INVENTION

The present invention relates to a method of cancer screening utilizing non-invasive or minimally invasive cell collection techniques, fluorescence detection techniques, and radio detection techniques. The invention herein also contemplates treatment of a cancer by various photo therapy treatments and/or radiation treatments.

The term "non-invasive" as used herein and as applied to a specific cell collection technique shall mean cell collection which does not involve the forced removal of tissue as by the act of cutting or otherwise tearing away cell tissue which would normally remain attached to the body. As discussed further below, a cell collection technique using a cytological brush would be considered non-invasive because, although contact is made with a targeted area of tissue to be removed, the cytological brush simply removes a top layer(s) of cells which would normally exfoliate or desquamate from the body. Thus, a cytological brush used according to the cell collection techniques of this invention does not involve the scraping of tissue to a degree that it cuts or tears tissue away from the body. The term "minimally invasive" as used herein and as applied to other cell collection techniques disclosed herein shall mean the removal of cells from the body which requires some interventional means for accessing the targeted group of cells, but does not require the actual tearing or cutting away of such targeted tissue. As discussed further below, minimally invasive cell collection techniques include the use of a fine gauge needle or catheter which must penetrate the body to gain access to interior targeted tissue. This minimally invasive cell collection technique is used specifically with the collection of cells from the central nervous system, peritoneal cavity, and thoracic cavity. Cell collection from these areas in the body is not achieved by cutting or tearing away the tissue, but is achieved by non-invasive means once the minimally invasive access procedure has taken place.

Thus, according to one aspect of the present invention, the exfoliation or dislodgement of cells from the human body is achieved through non-invasive means. For dislodgement of pulmonary system cells, techniques are disclosed which include fist percussion while a patient is placed in a postural drainage position. For exfoliation of gastrointestinal cells, the techniques include lavage cytology by oral administration of a first balanced electrolyte solution to cleanse the bowel which is followed by oral administration of an additional electrolyte solution to produce a clear anal effluent for cytologic evaluation. Cells in the oral cavity may be collected by a cytological brush. For prostate gland cell dislodgement, a physician may "milk" the prostate to express contained fluids which are carried through the ductal system to the urethra via the seminal vesicles and the ejaculatory ducts. For urinary tract cells, exfoliation may be achieved by rapid oral fluid intake and the use of a diuretic such as Lasix™. For collection of cervical and uterine cell samples, a cytological brush may also be used. For breast cell collection, the ductal system of the breast may be opened by the use of a product such as Ceruminex™ which dissolves "plugs" in the ducts of the nipple, and gravity is allowed to cause fluids to drain out. The discussion below more fully details these special non-invasive cell collection techniques. Collection of other cell types is also discussed below.

Once the targeted cells have been removed from the body, they are immediately placed in a temperature controlled (37° C.) cell culture solution or media to keep them alive a desired period of time. For most cells, a cell transport media is used which is identical to commercially available cell culture media. A water bath is typically used to maintain the culture at the desired temperature.

A photosensitive compound is then introduced to the cell culture. These compounds when administered in appropriate amounts selectively enter into pre-malignant and malignant cells, and provide a "fluorescent marker" in the cells, primarily in the mitochondria surrounding the nucleus. The compounds which may be used in this method to induce fluorescence include 5-ALA, protoporphyrin IX, tetrakis carboxy-phenyl porphine (TCPP), hematoporphyrine derivative, photofrin, and photofrin II and other known in the art to cause fluorescence in pre-malignant or malignant cells. For TCPP, this compound enters live cells via a special transport mechanism found in the outer cellular wall. TCPP will not enter dead cells, thus making it important that a live cell culture be maintained. Once inside the cell, TCPP appears to migrate to the perinuclear areas and become involved with the mitochondria. In short, the above compounds will cause pre-malignant or malignant cells to fluoresce when exposed to frequencies of light which match the excitation frequency of the particular compound used; however healthy cells will generally not fluoresce.

Once the photosensitive compounds are introduced to the cell culture, they are allowed to interact with the cell tissue a specified amount of time in a controlled environment. After this incubation period, cells may be examined by use of a fluorescence microscope to see if any cells fluoresce.

Fluorescence in the cell indicates a high degree of suspicion for malignancy. The cell culture can first be centrifuged to help separate the cells from the cell culture fluids. The cells are resuspended in saline, and a small aliquot is placed on a slide. If no cells are found to fluoresce after initial observation under the fluorescence microscope, the cells are disaggregated and processed through a flow cytometer utilizing fluorescence detection. This is done to ensure that no fluorescent cells are overlooked. Manual examination of cell suspensions is not particularly accurate, since millions of cells need to be examined. Flow cytometers can find a single fluorescent cell in a field of millions of cells with virtual 100% accuracy. The fluorescence microscope and the flow cytometer provide light to match the excitation frequency of the particular compound used. For example, the excitation frequency for TCPP is approximately 380–450 nanometers. If fluorescent malignant cells are found by the fluorescence microscope, they may also be counted and disaggregated for further study. After incubation, no further care of the cell specimen is required.

Alternatively, the above-described photosensitive compounds may be administered directly to the patient prior to cell collection. 5-ALA can be administered orally, topically, or parenterally (by injection); however, the other compounds have to be administered topically or by injection (parenterally). The waiting period prior to cell collection is then two to four hours, depending upon the compound introduced. After sufficient time has been provided for interaction between the compound and the targeted cells, the cells may then be exfoliated or dislodged from the patient through non-invasive or minimally invasive techniques.

In addition to providing the above described photo sensitive compounds alone, the photo sensitive compounds may be complexed with a radioisotope, such as $^{64}$Cu or $^{67}$Cu. Accordingly, these complexes then provide the ability for not only conducting fluorescence detection and phototherapy, but also provides the ability for observation of malignancies through positron emission tomography (for $^{64}$Cu) or single photon emission computed tomography (for $^{67}$Cu). Additionally, for $^{67}$Cu, it provides a source of beta radiation for selective destruction of malignancies. As well understood by those skilled in the art, positron emission tomography (PET) is a scanning technique which enables precise mapping of tissue which uptakes the radioactive marker. Single photon emission computed tomography (SPECT) is closely related to PET scanning and also provides an exact means to locate targeted tissue which uptakes an introduced radio tracer.

For those cells which are not dislodged through exfoliation and are therefore left within the body, those cells are doubly tagged not only for fluorescence, but for radioactivity as well. It may be, therefore, desirable under some circumstances to not only remove cells from the body for exuluo analysis, but also to investigate believed malignancies through fluorescence guided endoscopy, or to view the suspect cells through the appropriate tomography technique. One advantage of attaching a radioisotope to the photosensitive compounds is that through the use of recently available tomography devices one can, in effect, conduct a complete body scan of all potentially malignant areas within the body without having to conduct separate endoscopic procedures for each potentially malignant site found. The images taken from the scanning technique can then be provided to the particular specialist for follow-on treatment, which may include surgical intervention or radiation treatment.

By the method of this invention, a quick and reliable means is provided for cancer screening. Because non-invasive or minimally invasive techniques are used for cell collection, patient trauma is reduced along with the cost of the procedure. Because the method of this invention provides the option of introducing the compounds ex-vivo, the concern for any possible allergic reaction or phototoxic reaction by a patient's exposure to the sun is eliminated. Furthermore, because no tissue biopsies are taken, the method of this invention eliminates the inherent hazard in administering local and/or general anesthesia. Cell marking by use of the above-identified compounds is extremely reliable in terms of differentiating healthy cells from pre-malignant or malignant cells. The segregation, counting and analysis of the fluorescent cells may be achieved with commercially available flow cytometers and supporting equipment. The results of the cancer screening procedure may be forwarded to a pathologist who may wish to conduct additional tests to further determine the exact nature of the malignancy. The fluorescing cells may be photographed to provide documentation of malignancy.

The method of the invention also provides the option of utilizing radioactively tagged photo-sensitive compounds, wherein fluorescence guided endoscopy can be conducted for viewing and treatment of a malignancy, and additionally, the radioactive tag allows various tomography techniques to be used for further visualization of potentially malignant tissue as well as providing a means for radioactive treatment. These and other advantages are discussed more fully below in the detailed description taken in conjunction with the corresponding figures.

BRIEF DESCRIPTION OF THE DRAWINGS

FIGS. 2A and 2B are organizational diagrams illustrating both the types of cells which may be exfoliated or collected according to the cell collection techniques of this invention, and the major steps in the various cell collection techniques; and FIG. 3 is another simplified flow diagram illustrating the major steps in another aspect of the invention including use of porphyrin complexes for radio tracing and radiation therapy.

DETAILED DESCRIPTION OF THE INVENTION

Figure 1:
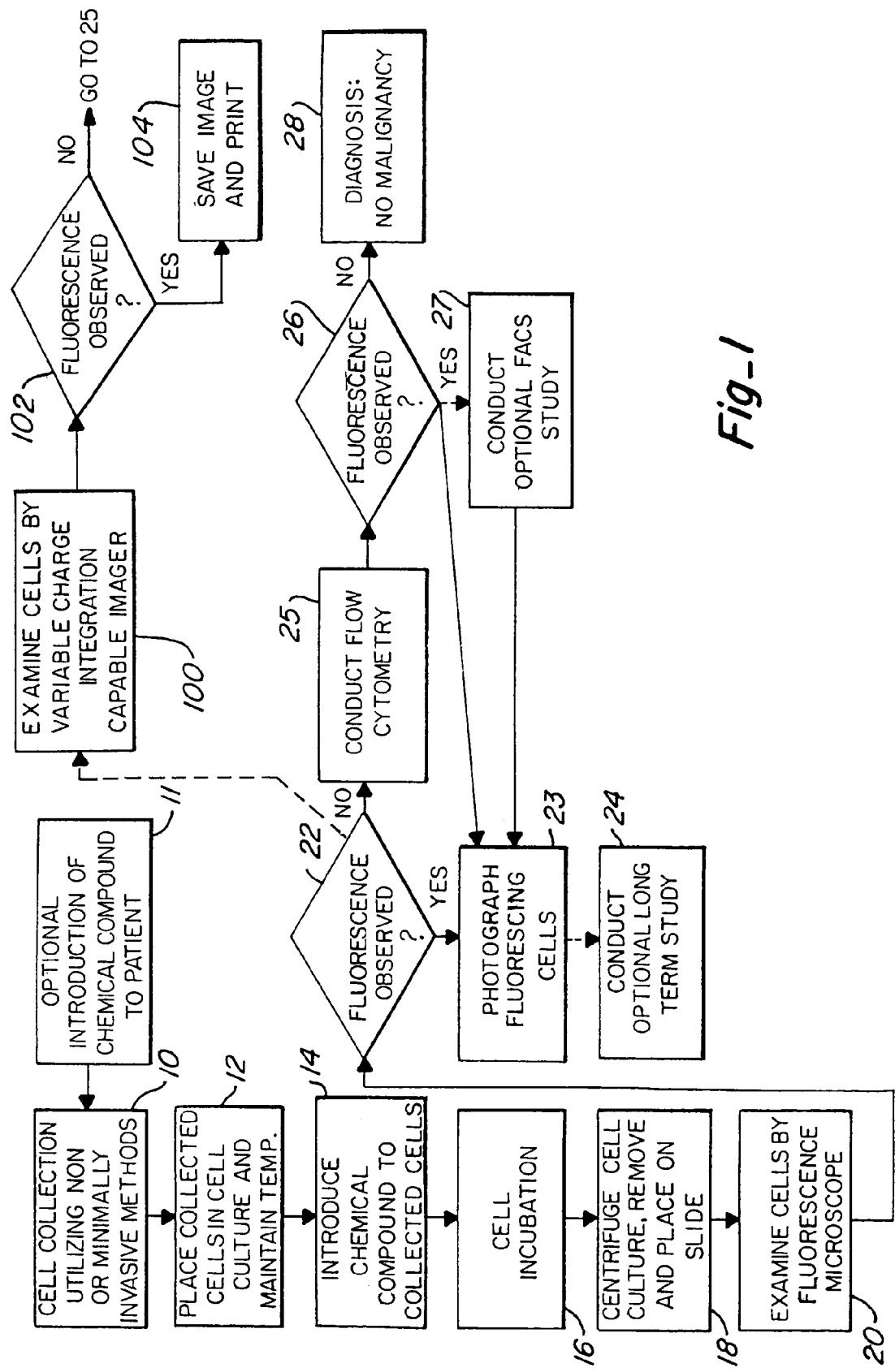
FIG. 1 is a simplified flow diagram illustrating the major steps in one aspect or part of the method of this invention.

FIG. 1 illustrates the major steps in one aspect of the method of this invention. As shown, the process begins with non-invasive means or minimally invasive means of cell exfoliation/collection 10. Once collected, the cells are then placed in a culture media or cell transport media, shown at step 12. The goal is to keep the collected cells alive and viable after removal from the body. Thus, even at this intermediate step, the cells should be maintained at approximately 37° C. by use of a water bath or other means. Next, the collected cells are exposed to a chemical which induces fluorescence in pre-malignant and malignant cells, illustrated as step 14. As discussed above, the chemical compounds which are contemplated for use in this invention include, but are not limited to, 5-ALA, protoporphyrin IX, TCPP, hematoporphyrin derivative, photofrin, and photofrin II. Other possible compounds which may be used include uroporphyrin; coproporphyren; tetraphenylporphine-sulfonate (TPPS); and tetraporphen (4, N-methyulpyridil)

(TMPP). These compounds, when administered in appropriate amounts, selectively enter pre-malignant and malignant cells, and provide a fluorescent marker inside the cell, primarily in the mitochondria surrounding the nucleus. Of special utility is the compound TCPP. This compound is available from Porphyrin Products, P.O. Box 31, Logan, Utah. As best understood, TCPP enters a live cell via a special cell transport mechanism in the outer cellular wall. TCPP will not enter a dead cell. Once inside the cell, the TCPP migrates to the perinuclear areas and becomes involved with the mitochondria. TCPP is not a stain as used in a Pap smear or other similar procedures. Therefore, it is imperative that this compound be utilized for fluorescent tagging of cells prior to cell death. For ex-vivo introduction of the chemical compound, the preferred compound is TCPP.

In terms of cell storage in the culture media, commercially available cell culture media may be used to keep the cells viable. These solutions contain nutrient materials as well as selected antibiotics to counteract any infective organisms which might alter capabilities of the cell to effectively interact with the introduced chemical. Immediately after removal from the body, the cells are placed in the nutrient solution or cell transport media. For example, the cell samples may be placed in a commercial medium known as "Dulbecco's Modified Eagles Medium," which is supplemented with a 10% calf serum, penicillin and streptomycin at standard tissue culture concentrations. This medium is well known in cell culture laboratories and readily available commercially or may be formulated in the cell culture laboratory by technicians.

After introduction of the chemical to the cell culture, the culture is incubated for a specified amount of time which allows the live cells to absorb and interact with the compound, shown as step 16. In test trials, it has been found that a 1–4 hour incubation time is needed for pre-malignant and malignant cells to interact with the compounds. The average time for incubation for TCPP is 1–2 hours. The cells are maintained in a culture incubator by use of the water bath at approximately 37° C. The incubator may utilize air containing 5% carbon dioxide which surrounds the water bath. These cell suspensions contain both non-malignant, and (in some cases) malignant cells. Normal cells are difficult to keep alive in cell culture, and generally die in seven to 10 days from time of removal from the body regardless of the care taken in trying to maintain their survival. Malignant cells, on the other hand, can generally be kept alive in cell culture situations for several weeks or months. During this early incubation period, it is also advisable to agitate the cell cultures at frequent intervals to make sure that the compound comes into contact with all cells contained within the cell culture container.

After adequate interaction has occurred between the introduced chemical compound and the cells within the culture, the cells need to be prepared for first observation. Accordingly, the cell suspension is placed in a centrifuge tube and the cell sample is centrifuged. The cells become concentrated at the bottom of the centrifuge tube in a "button" of cells. The cell culture media fluid is then removed by pouring off all but about 10% of the fluid. The remaining cell culture media is then removed with a pipette, and the cells are resuspended in a saline solution. Small amounts of resuspended cells are then removed with a pipette (e.g., one to two gtts) and placed on a glass slide with a slide cover. These preparation efforts are generally indicated at block 18.

The cells are then observed under a fluorescence microscope. The fluorescence microscope can be tuned to provide light which matches the excitation frequency. For TCPP, the excitation frequency ranges from 380–400 nanometers. The technician observing the cells under the fluorescence microscope looks for cells which fluoresce in the visible red range (approximately 630 nanometers). The step of examining the cells and providing a matching excitation frequency for observation of characteristic fluorescence is shown at block 20. If a compound other than TCPP is used, the fluorescence microscope is tuned to provide the matching excitation frequency, and observation is made for the characteristic fluorescence. There are a number of commercially available fluorescence microscopes which may be used in the method of this invention. Some of the manufacturers of such devices include Olympus, Nikon, and Karl Zeiss. If any cells fluoresce, then this would be an indication of malignancy. This is shown at decision point 22 wherein the next step would be color photography of the fluorescing cells for documentation purposes, shown at block 23. Optionally, long-term cell observation could be conducted wherein the cells would be placed back into a culture media for additional studies. This is shown at block 24.

If no fluorescing cells were found with the initial observation under the fluorescence microscope at block 20, then, as also shown at decision block 22, the cells then undergo further analysis to determine whether there are any malignant cells present. Although the use of a fluorescence microscope would allow an observer to find larger numbers of malignant cells, this is not an absolute test for finding fluorescing cells. Accordingly, these cells would be processed through a flow cytometer to find and count fluorescing cells. This is shown at block 25. If the flow study reveals any fluorescing cells, this would be an indication of malignancy. As shown at block 27, the specimen could then prepared for fluorescence activated cell sorting. Fluorescence activated cell sorting (FACS) is done to further concentrate the specimen of fluorescing cells for easier observation and is an additional function which may be incorporated within a flow cytometer. Fluorescence activated cell sorting is achieved based upon the presence or absence of fluorescence by a particular cell. By use of one of the compounds discussed above, the cells which are pre-malignant or malignant will fluoresce while non-malignant cells will not. Accordingly, fluorescence activated cell sorting can effectively separate out in a very precise manner pre-malignant and malignant cells versus non-malignant cells. Once the FACS study is complete, the fluorescing cells are segregated from the remaining cells which do not exhibit fluorescence. This concentrated sample of fluorescing cells then may be viewed under a fluorescence microscope and photographed. The presence of even one fluorescing cell can be cause for making a screening diagnosis of cancer. If no fluorescing cells are found, then the screening diagnosis is no malignancy, shown at block 28. Optionally, a long-term study of the fluorescing cells found at block 25 may also be conducted.

Although the above procedure describes the step of conducting a FACS study, it should be understood that, in those instances in which no fluorescing cells are found under initial observation at block 20, a screening diagnosis of a malignancy can actually be made once the cells are processed through the flow cytometer and fluorescent cells are found and counted. As discussed above, the main reason that the FACS study is conducted is to better concentrate the fluorescing cells within a smaller sample size. Otherwise, finding the cells under the fluorescence microscope and photographing the cells would be much more difficult.

It should also be understood that the collection of cells by the minimally/non-invasive methods discussed below may result in an extremely large number of cells being collected. For example, a specimen submitted from the uterine cervix collected by use of the cytology brush explained below, on the average, collects approximately 5 million cells. A careful manual examination of 5 million cells would take several days. Accordingly, in instances such as these where there are such a large number of cells, the first observation step at block 20 would be conducted by using several slides and observing them in the fluorescence microscope. If no fluorescing cells were found, the remainder of the specimen can then be processed through the flow cytometer. As desired, a FACS could also be conducted.

Depending upon the size of the sample which is taken from the body, the collected cells within the specimen could be processed on a standard flow cytometer even prior to initial observation under the fluorescence microscope. In the case of large volumes of fluid contained within a cell culture, such as one would obtain on a screen for uterine cervix or colon cancer, a flow cytometer can process large volumes of cells in a very short period of time. Commercially available flow cytometers may be used. Manufacturers of such devices include Coulter, Becton-Dickenson, and Cytomation. As well understood in the art, flow cytometry involves the suspension of individual cells in a solution, then moving the cells through a tubular system which only allows one cell at a time to flow. The cells pass through a chamber in the system where there is a selection of lasers of selected different frequencies of light to conduct a number of measurements to include cell counts, cell measurements as to overall size and other parameters. As applied to the method of this invention, the flow cytometer would have a selection of lasers which provide light to match the excitation frequency of the particular compound used to produce fluorescence in the cell sample. By this fluorescent tagging, the flow cytometer is able to accurately count the number of cells which fluoresce. In order to actually separate fluorescing versus non-fluorescing cells, the FACS must be conducted. The FACS involves the inducement of a charge (positive or negative) on the cell surface of each cell which passes through the flow cytometer. By this induced charge, the fluorescing cells are separated from non-fluorescing cells. Accordingly, the fluorescing cells would be placed into a separate container from the non-fluorescing cells. As discussed above, this concentrated sample of fluorescing cells makes viewing easier under a fluorescence microscope, and for easier photographing of the fluorescing cells. Because the use of a flow cytometer and the additional step of conducting a FACS involves the use of sophisticated and fairly expensive equipment, in most cases, it is desirable first to attempt to locate fluorescing cells by simply viewing them under a fluorescence microscope. However, it shall be understood that the method of this invention is not limited to any particular sequence in terms of using a flow cytometer, a fluorescence microscope, or conducting a FACS. Thus, it is conceived within the spirit and scope of this invention that a FACS could be conducted immediately after the cell sample was centrifuged. However, since the great majority of tests conducted will yield a conclusion of no cancer, it is not advisable to immediately move to either flow cytometry or conducting a FACS without first manually observing the cell sample through a fluorescence microscope. The capabilities of flow cytometers and fluorescence activated cell sorters are well known to those trained in the field.

As also shown in FIG. 1, introduction of the desired chemical compound for purposes of creating fluorescing cells can alternatively be achieved by introducing the compound to the patient prior to cell collection. This option is illustrated at block 11. As discussed above, the compound 5-ALA may be introduced to the patient orally, topically, or parenterally. The other compounds listed may only be given parenterally or topically.

The collected cells may be also placed in culture for observation over a longer period of time. In general, normal non-malignant cells will survive a much shorter period of time in comparison to malignant or neoplastic cells. This extended observation of the collected cells can be used as a confirmative test of the initial screening diagnosis.

Generally speaking, individual physician offices do not have fluorescence microscopes or other equipment which would be used to analyze the cells in the cell cultures. Accordingly, the cell cultures would be transported to a regional laboratory for examination by a laboratory technician and a physician. These individuals now perform standard screenings for conventional Pap smears and other cancer screening procedures.

As disclosed in Kennedy, et al., U.S. Pat. No. 5,211,938, 5-ALA is a significantly different compound compared to standard porphyrins in that it, by itself, 5-ALA is not a fluorescent marker, but is a precursor to a fluorescent marker, namely, protoporphyrin IX. When 5-ALA is administered, it enters a metabolic pathway within the cell and is converted to PPIX, which is an immediate precursor of heme. 5-ALA may be administered orally, topically, or by parenteral administration. 5-ALA is taken up by virtually all nucleated cells, and quickly enters into the "heme" synthesis pathway, eventually resulting in the transformation into PPIX. In non-malignant cells, the process is blocked by a built-in cellular feedback mechanism which effectively stops all PPIX formation. However, the feedback mechanism in malignant cells and those in rapid cell division (characteristic of many pre-malignant cells) is not operational, and PPIX is produced in significant quantities. 5-ALA is available from a manufacturer, Sigma Chemical Co., St. Louis, Mo. At the present time, 5-ALA is sold as a reagent worldwide, and not as a USFDA (Food and Drug Administration) approved drug; however, this may change since applications are in process to use 5-ALA in photo therapy.

Flow cytometers may also be used not only to count fluorescing cells, but also to measure various dimensions of cells including overall cell diameter, nuclear size, chromatin material in nucleus, cytoplasmic structures such as mitochondria, and others. Cells may thus be sorted on the basis of overall cell size. Flow cytometers can also be programmed to count cells of a specific size, and provide overall counts of such cells in a total specimen. A flow cytometer can also be programmed to sort out and tabulate data on any type of cell from a whole host of cells in various cell suspensions. It is also understood by those skilled in the art that flow cytometers can do other sophisticated studies on the cells such as ploidy studies to determine the chromatin content of the nuclei (diploid cells have the correct number and size of chromosomes while aneuploid cells are those that have significant alterations in chromosome content). These very exacting measurements can be done at rates of thousands of cells per second.

In some circumstances, it may be necessary to provide some pre-separation of the collected cells. For example, based upon the collection techniques discussed above, some cells will be removed in clumps or sheets of cells. In order to ensure that these clumps or sheets of cells are completely exposed to the compound used as the fluorescent marker, the cells must be separated. Well known laboratory procedures exist for separation of these clumps or sheets of cells through use of certain enzymes, chelating agents, and even mechanical separation by high speed centrifugation followed by dilution in low viscosity solutions. These methods of cell "disaggregation" are well known in cell sorting laboratories.

Once the fluorescing cells are identified, the cells can be saved for further examination by a trained pathologist. Ultimately, a pathologist makes a diagnosis as to the presence of a malignancy. If it is determined that the collected cells are malignant, the prior art methods may then be used to locate and remove the tumor (such as described in Kennedy, et al., U.S. Pat. No. 5,211,938), or the tumor may then be located and removed by fluorescence guided endoscopic surgery, utilizing endoscopes and surgical devices under guidance of fluorescence. If it is determined that open surgery is required to remove a tumor, fluorescence assisted surgery can also be conducted under these circumstances wherein the surgeons utilize headlights capable of delivery of tuned frequencies of light, and other light emitting equipment may be used, such as retractors, probes, and dissectors with built-in illumination.

The method of this invention primarily utilizes cells which normally desquamate from the various surfaces of the body, both internal and external, thus their removal by non-invasive means does not result in undue patient trauma. These non-invasive cell collection methods accelerate the release of such cells from the surfaces of the tumor mass, and then, as described above, are collected and analyzed.

FIGS. 2A and 2B illustrate organizational diagrams of the types of cells which may be removed according to these non-invasive and minimally invasive methods, and also shows the major steps or actions which are used to collect the types of cell. As shown, cell collection 10 may be achieved with cells from the pulmonary system 30, prostate gland 32, cervical/uterine area 34, breast 36, oral areas 38, urinary tract 40, gastrointestinal tract 42, central nervous system 43, and a miscellaneous group 45.

The specific types of cells which may be exfoliated are as follows:

1. Pulmonary system 30—trachea, bronchi, bronchioli, and alveoli.
2. Prostate gland 32—seminal vesicles and ejaculatory ducts.
3. Cervical/uterine area 34—uterus, cervix and uterine cavity cells.
4. Breast 36—ductal carcinoma cells.
5. Oral 38—all cell types exposed in the mouth to include cheek lining, tongue, floor and roof of the mouth, gums and throat.
6. Urinary tract 40—kidney, pelvis, calyces, ureters, urinary bladder, and urethra.
7. Gastrointestinal tract 42—esophagus, stomach, small intestine, and large intestine (colon).
8. Central nervous system 43—ventricles and meninges.

In addition to the general cell categories discussed above, there are other cells within the body which may be removed by the non-invasive or minimally invasive techniques. This miscellaneous group is shown as group 45 which includes cells from the peritoneal cavity 64 such as liver, pancreas, ovaries, and other peritoneal cells, and cells from the thoracic cavity 66 such as pleurocentesis cells. Also included from this miscellaneous group are cells within the sinus and nasal system 68 and auditory canal 70.

Now, a discussion will follow which more particularly points out the non-invasive and minimally invasive techniques of cell collection for each of the groups of cells.

Block 44 lists the major actions conducted in collecting cells from the pulmonary system 30. As shown, this non-invasive collection technique includes fist percussion while a patient is placed in a postural drainage position, and then postural drainage allows cell laden respiratory fluid to be captured. Sputum, by itself, does not generally contain pulmonary cells which come from the lining of the air ducts within the lung (bronchi and alveoli cells). Therefore, the postural drainage in conjunction with the fist percussion helps to dislodge pulmonary cells to create a cell laden fluid with bronchi, alveoli, and the other cells listed above. The patient is placed on the edge of a bed or other horizontal surface with the hips and legs horizontal, and the chest and head hanging down to the floor. This postural drainage position allows secretions from the alveoli, bronchi, and trachea to flow by gravity through the trachea toward the mouth. Repeated fist percussion over the entire chest wall helps to continue the dislodgement of cells and to continue the flow through the trachea to the mouth. Coughing at intervals also allows for collection of large numbers of cells during postural drainage.

For exfoliation of prostate cells 32, the non-invasive collection method is achieved simply by "milking" the prostate gland. This is shown at block 46. A physician would simply conduct a digital rectal examination to determine the status of the gland. The gland is "milked" by squeezing the gland to express contained fluids. These fluids are carried by the ductal system to the urethra via the seminal vesicles and ejaculatory ducts.

For exfoliation of cervical and uterine cells 34, non-invasive collection can be carried out by use of a cytology brush, shown at step 48. One example of a cervical collection brush which can be used is disclosed in my earlier U.S. Pat. No. 4,762,113. The cytology brush disclosed in this patent has proven to be superior to standard cytological brushes in its ability to collect the necessary quantity of cells.

For exfoliation of cells from the breast 36, the patient is placed in a face down position with both breasts dropping down through apertures in an examination table top. This allows both breasts to hang, unsupported, through the table top. The ductal system of the breasts can then be opened by use of a product such as "Ceruminex™." Gravity allows fluids retained within the breast ductal system to drain out through the ducts in the nipple. To accelerate fluid removal, a commercially available breast pump could be used, such as that used by nursing mothers. This non-invasive method is shown at block 50.

In order to obtain cells from the mouth or throat area, a cytological brush may be used which brushes the suspicious areas. This non-invasive technique is shown at block 52. The cervical collection brush mentioned above is also ideal for use in removal of cells in the mouth and throat.

In order to exfoliate cells from the urinary tract 40, rapid oral fluid intake in conjunction with administration of diuretics such as Lasix™ results in cell exfoliation from the transitional cell linings of the urinary tract. Fluids are collected from the urethra, and some fluids may be washed out further by the act of urination. This very rapid flow, occurring at the level of the renal pelvis and continuing through the ureters, bladder, and urethra will dislodge cells in large quantities. The cells can then be collected, concentrated by centrifugation, and preserved in the cell transport media of the cell culture. This method is shown at block 54.

In order to collect cells from the gastrointestinal tract 42, lavage cytology is utilized by first giving the patient an orally administered balanced electrolyte solution. The solution may include drugs which increase bowel evacuation, such as biscodyl, colyte, and golytely. This first application of an electrolyte solution induces a cleansing wash of the bowel to remove fecal materials. Then, an additional orally administered electrolyte solution can be given to the patient to produce a clear anal effluent for cytological evaluation. This clear fluid contains thousands of cells, and if a malignancy exists, cancer cells will be washed out with the large volume of fluid. This technique is shown at block 56.

Cells can be collected from the central nervous system 43 by conducting a "tap" of the spinal canal with a syringe and needle used in standard spinal tap procedures. Thus, for this type of cell collection, non-invasive means for cell exfoliation is not possible. This technique for removal of cells from the central nervous system 43 is shown at block 72.

Non-invasive means are also not available for removal of cells from both the chest (thoracic) cavity 66 and the peritoneal cavity 64. A minimally invasive means of cell collection for these types of cells may be achieved by utilizing a syringe and needle or using a peritoneal lavage catheter. A syringe and needle or a catheter inserted through a needle is placed in the cavity. Fluids are introduced into the cavity to dislodge cells, and then the cell laden fluid is removed from the cavity for collection. This involves the use of normal saline irrigations via the catheter (a wash of peritoneal cells). As necessary, the cells are centrifuged and immediately placed in the cell transport media. This technique is identified as blocks 76 in FIG. 2.

To induce exfoliation for cells in the auditory canal 70 or the nasal area and sinus passages 68, a cytologic brush may be used. The brush is inserted into the ear or nose and placed in contact with the targeted area. This method is shown at blocks 74 of FIG. 2B. The cervical cytological brush mentioned above may also be used to collect cells from these areas.

One very clear example of the advantages of the method of this invention over standard cancer screening procedures is with relation to screening for prostate cancer. The typical procedure for prostate cancer screening is for the urologist to conduct a digital rectal examination which amounts to a "feel" of the prostate for areas of increased hardness within the gland. There are very many other reasons for hard lumps in the prostate gland including stones, fibrosis from prior infection, cysts, and infarction from loss of blood supply to a given segment of the gland. In addition, the urologist may order a study of acid phosphatase levels (a substance which may be elevated in the presence of a prostate cancer), and may order a study of prostate specific antigen levels (PSA) levels. Pelvis and abdominal x-rays may be used to determine if there are signs of bone metastasis. Ultrasound studies may be used to determine if there are any suspicious areas in the prostate gland. Each of the foregoing studies are presumptive tests, but none are absolutely diagnostic of prostate cancer. Even when these tests are performed, multiple needle biopsies are done which attempt to find cancerous areas in the gland. In short, the above-identified procedures are costly, can cause trauma to the patient, and do not necessarily provide for an early diagnosis. By comparison, the method of this invention is a relatively absolute diagnosis of a cancer. Although a pathologist may still wish to confirm the results of the screening test of this invention, the screening test of this invention greatly eliminates many costly procedures and greatly streamlines early cancer diagnosis.

In another aspect of the present invention, in addition to having the capability to screen cancer via fluorescence detection, it would also be desirable to simultaneously conduct the cancer screening investigation through another means which tags or identifies potentially malignant cells. In accordance therewith, the present invention also includes attaching a radioactive tag to the 5-ALA or other photo sensitive compound used, thereby providing medical personnel not only the ability to conduct the cancer screening by fluorescence detection, but also through a selected form of tomography.

The radioactive tag, which may be attached to the photo sensitive compound, includes such radio isotopes such as $^{64}$Cu or $^{67}$Cu. These radioisotopes are tightly complexed with most porphyrins. Additionally, certain radioisotopes of zinc are also tightly complexed to porphyrins.

If a complex such as PPIX-CU is administered to a patient having a suspected malignancy, the PPIX localizes in malignant cells, carrying the radioactive tag along. Since the malignant cells preferentially accept the PPIX, there is also the automatic acceptance of the radioactive copper molecule as well. Once the cancer screening has taken place through the non-invasive or minimally invasive means, the cells which do not exit the body due to the exfoliation process are left behind and are double tagged with fluorescence as well as radioactivity.

One reference which discloses a method of using radio tagged porphyrins is U.S. Pat. No. 5,391,547 to Cole et al. This reference is hereby incorporated by reference in its entirety.

The $^{67}$Cu provides a source of beta radiation for destruction of malignant tissue through radiation therapy, and $^{67}$Cu also emits gamma radiation which can therefore be used in SPECT. For $^{64}$Cu, this lighter isotope of copper is a positron emitter, and although it does not provide the opportunity for radiation treatment, $^{64}$Cu is a positron emitter which enables screening by PET techniques.

A PET or SPECT scan, done in addition to analysis of the fluorescening tissue, provides further substantial evidence regarding a malignancy, and the exact location of the major cancer site as well as metastatic sites. This radioactive tagging of the malignant tissue also provides the ability for a surgeon to better conduct a fluorescence type endoscopic procedure, because the PET or SPECT scan provides detailed mapping of suspected malignant areas. Thus, in all aspects of conducting investigational procedures, as well as treatment, the combination of a fluorescent tag and a radioactive tag is advantageous.

The metaloporphyrin complexes of the present invention can be administered to a patient alone or in combination with pharmaceutically acceptable carriers, the proportion of which is determined by the solubility and chemical nature of the compound and standard pharmaceutical practice. The physician will determine the ultimate dosage of these agents which will be most suitable for prophylaxis or treatment and will vary with the form of administration and the particular compound chosen, and also, with the particular patient under treatment. The physician will generally aim to initiate treatment with the lowest dose that will be cytotoxic to the malignant or pre-malignant cells. For the radioactive compounds of the present invention, the dose is measured by the radioactivity emitted by the compound. Thus, the weight of the metaloporphyrin and the coordinated metal is not used in determining the proper treatment dosage. For most patients, the range of dosages which effectively kill any malignant or premalignant cells in a site selective manner is between about 5 Gy and 25 Gy of radiation. Typically, the range is between about 9 Gy and about 18 Gy. Preferably, the range is between about 15 Gy and about 20 Gy.

One example of an investigational procedure which lends itself well to the method of this invention would be screening for a suspected bowel cancer. First, the screening procedure would be conducted by administering to the patient 5-ALA, and then using a non-invasive method to check exfoliated cells for fluorescence. If fluorescence is observed, malignant cells left inside the colon are tagged with both the fluorescent marker as well as the radioactive tag. PET scanning or SPECT scanning could then be conducted to determine the exact location of any sites of cancer located not only the bowel, but throughout the entire body. These locations would include the basic cancer site in the bowel, as well as additional sites of extension of the tumor, for example, through the wall of the bowel, and any other metastatic sites such as in the liver, lymph nodes, and lung. Once the scan has been reviewed, it is then possible to pass a fluorescence endoscope into the bowel to find the specific locations shown on the scan.

Another example of a type of cancer which is well suited for identification and treatment by the method herein is breast cancer. The introduction of 5-ALA to the patient tagged with a radioisotope can be used to not only examine cells from the breast removed by exfoliation, but can also provide a scan of both breasts outlining any sites of primary cancer. A surgeon looking for the tumor or tumors has the additional advantage of having fluorescence of the lesions which would aid the surgeon in locating and resecting all tumor sites.

Use of a dual tagging mechanism has a number of options in terms of not only identification of malignancies, but also treatment options. Referring now to FIG. 3, some of these investigational and treatment options are illustrated. Beginning first with block 100, the patient is provided the radio tagged compound. The specified period of time is then given to allow cell uptake of the compound, shown at block 102. In block 104, the cell collection is undertaken utilizing either the non or minimally invasive methods. The exfoliated cells are then examined by a fluorescence microscope shown at block 106. At block 108, if fluorescence is observed, then tomographic scanning can be conducted, shown at block 110. If there is no fluorescence observed, then flow cytometry can be conducted, shown at block 112. If at decision block 114, fluorescence is observed after conducting the flow cytometry, then the tomographic scanning can be conducted, as shown at block 110. If no fluorescence is observed, then there is presumptive conclusion of no malignancy, shown at block 116.

If the scanning has taken place, the treating physician then has a number of options. One option would be to conduct fluorescence guided endoscopy in order to further pinpoint the location of the malignancies, as shown at block 118. During the same procedure, the doctor would also have the option of conducting radiation therapy, shown at block 120, and of course, the doctor could also conduct the radiation therapy without first conducting the fluorescence guided endoscopy. The treating physician would also then have the option of conducting the necessary surgical procedure, shown at block 122, and/or the physician could simply conduct further observation, shown at block 124.

A number of variations to the methodology shown in FIG. 3 can be used to achieve useful results in combining a fluorescence tracer and radio tracer. For example, tomographic scanning could be conducted prior to fluorescence observation. Thus, the scanning would be considered the first phase in the investigation and the fluorescence observation would be considered the second or confirmatory phase in the investigation.

Utilizing two separate means for identification and treatment of a cancer has the many advantages as discussed above. The use of a compound which results in fluorescing cancerous tissue allows medical personnel to pinpoint cancerous areas, and provides many options in treating the cancer, which would include not only photo-dynamic therapy, but other traditional modes of treatment. Attaching a radioactive tag to the compound provides yet another dimension for identification and treatment of the cancer. The radioactive tag further allows medical personnel to accurately locate, and then provide additional treatment. The advances in SPECT and PET scanning enables a treating physician to map and record the coordinates of cancerous tissue for subsequent treatment.

This invention has been described in detail with reference to particular embodiments thereof, but it will be understood that various other modifications can be incorporated within the spirit and scope of the invention.

What is claimed is:

1. A method of cancer screening comprising the steps of:
    administering a compound to a patient for uptake into target cells, the compound having a fluorescent marker portion, and a radioactive portion in target cells, wherein said fluorescent marker portion is selected from the group consisting of 5-ALA, protoporphyrin IX, TCPP, hematoporphyrin derivative, photofrin, uroporphyrin, coproporphyrin, TPPS, and TMPP, and said radioactive portion is a radioisotope of copper;
    collecting the targeted cells from the patient;
    stimulating the collected targeted cells with a frequency of light that will cause pre-malignant and malignant cells to fluoresce;
    conducting tomographic scanning of the patient after the stimulating step if fluorescence is observed; and
    conducting radiation therapy by site selective ionizing radiation treatment from said radioactive portion of said compound wherein the compound is administered in a dose emitting between about 5 Gy and 25 Gy radiation.

2. A method, as claimed in claim 1, further including the step of:
    conducting fluorescence guided endoscopy for further observation or treatment of areas found during the first conducting step.

3. The method of claim 1, wherein the compound is administered in a dose emitting between about 9 Gy and about 18 Gy radiation.

4. The method of claim 1, wherein the collected targeted cells are disaggregated prior to the stimulating step.

* * * * *